(12) United States Patent
Banerjee et al.

(10) Patent No.: US 12,016,705 B2
(45) Date of Patent: Jun. 25, 2024

(54) METHODS AND SYSTEMS FOR IDENTIFYING PRESENCE OF ABNORMAL HEART SOUNDS OF A SUBJECT

(71) Applicant: Tata Consultancy Services Limited, Mumbai (IN)

(72) Inventors: Rohan Banerjee, Kolkata (IN); Avik Ghose, Kolkata (IN)

(73) Assignee: TATA CONSULTANCE SERVICES LIMITED, Mumbai (IN)

(*) Notice: Subject to any disclaimer, the term of this patent is extended or adjusted under 35 U.S.C. 154(b) by 939 days.

(21) Appl. No.: 17/060,009

(22) Filed: Sep. 30, 2020

(65) Prior Publication Data

US 2021/0298688 A1    Sep. 30, 2021

(30) Foreign Application Priority Data

Mar. 28, 2020   (IN) .............................. 202021013675

(51) Int. Cl.
*A61B 5/00* (2006.01)
*A61B 5/02* (2006.01)
(Continued)

(52) U.S. Cl.
CPC ........ *A61B 5/7282* (2013.01); *A61B 5/02028* (2013.01); *A61B 5/725* (2013.01);
(Continued)

(58) Field of Classification Search
CPC .......... G06N 3/0895; G06N 3/00; G06N 3/02; G06N 3/08; A61B 5/725; A61B 5/7267; A61B 7/04; G16H 50/20
See application file for complete search history.

(56) References Cited

U.S. PATENT DOCUMENTS

2020/0372654 A1*  11/2020  Kohl .......................... G06T 7/11
2021/0169442 A1*   6/2021  Agarwal ................ A61B 5/7264
(Continued)

OTHER PUBLICATIONS

Liao, Weixian et al., "A Unified Unsupervised Gaussian Mixture Variational Autoencoder for High Dimensional Outlier Detection", International Conference on Big Data (Big Data), 2018, IEEE, https://www.researchgate.net/publication/330625995_A_Unified_Unsupervised_Gaussian_Mixture_Variational_Autoencoder_for_High_Dimensional_Outlier_Detection/link/5c845d1392851c695067f5ef/download.
(Continued)

*Primary Examiner* — Tan H Tran
(74) *Attorney, Agent, or Firm* — FINNEGAN, HENDERSON, FARABOW, GARRETT & DUNNER, LLP

(57) ABSTRACT

The disclosure generally relates to methods and systems for identifying presence of abnormal heart sounds from heart sound signals of a subject being monitored. Conventional Artificial intelligence (AI) based abnormal heart sounds detection models with supervised learning requires a substantial amount of accurate training datasets covering all heart disease types for the training, which is quiet challenging. The present methods and systems solve the problem solves the problem of identifying presence of the abnormal heart sounds using an efficient semi-supervised learning model. The semi-supervised learning model is generated based on probability distribution of spectrographic properties obtained from heart sound signals of healthy subjects. A Kullback-Leibler (KL) divergence between a predefined Gaussian distribution and an encoded probability distribution of the semi-supervised learning model is determined as an anomaly score for identifying the abnormal heart sounds.

9 Claims, 9 Drawing Sheets

(51) Int. Cl.
    *A61B 7/04*      (2006.01)
    *G06N 3/00*      (2023.01)
    *G06N 3/02*      (2006.01)
    *G06N 3/045*      (2023.01)
    *G06N 3/08*      (2023.01)
    *G06N 3/088*      (2023.01)
    *G16H 40/67*      (2018.01)
    *G16H 50/20*      (2018.01)
    *G16H 50/30*      (2018.01)

(52) U.S. Cl.
    CPC .......... *A61B 5/7257* (2013.01); *A61B 5/7267* (2013.01); *A61B 5/7278* (2013.01); *A61B 7/04* (2013.01); *G06N 3/00* (2013.01); *G06N 3/02* (2013.01); *G06N 3/045* (2023.01); *G06N 3/08* (2013.01); *G06N 3/088* (2013.01); *G16H 40/67* (2018.01); *G16H 50/20* (2018.01); *G16H 50/30* (2018.01)

(56) References Cited

U.S. PATENT DOCUMENTS

2021/0304855 A1*   9/2021   Ansari ................ A61B 5/7275
2022/0249031 A1*   8/2022   Clifton ................ A61B 5/7264

OTHER PUBLICATIONS

Yang, Chao et al., "AutoTag: Recurrent Variational Autoencoder for Unsupervised Apnea Detection with RFID Tags", Global Communications Conference (GLOBECOM), 2018, IEEE, http://www.eng.auburn.edu/~szm0001/papers/AutoTag_journal.pdf.

Ghimire, Sandesh et al., "Generative Modeling and Inverse Imaging of Cardiac Transmembrane Potential", Computer Science, Engineering, Mathematics, 2018, ArXiv, https://www.researchgate.net/publication/333077512_Generative_Modeling_and_Inverse_Imaging_of_Cardiac_Transmembrane_Potential/link/5cee6659a6fdcc3db82e7eee/download.

Painchaud, Nathan et al., "Cardiac MRI Segmentation with Strong Anatomical Guarantees", Computer Vision and Pattern Recognition (cs.CV,), 2019, ArXiv, https://arxiv.org/pdf/1907.02865v1.pdf.

* cited by examiner

METHODS AND SYSTEMS FOR IDENTIFYING PRESENCE OF ABNORMAL HEART SOUNDS OF A SUBJECT

PRIORITY CLAIM

This U.S. patent application claims priority under 35 U.S.C. § 119 to: Indian Patent Application No. 202021013675, filed on 28 Mar., 2020. The entire contents of the aforementioned application are incorporated herein by reference.

TECHNICAL FIELD

The disclosure herein generally relates to monitoring of heart sound signals, and, more particularly, to methods and systems for identifying presence of abnormal heart sounds in the heart sound signals of a subject being monitored.

BACKGROUND

Abnormal heart sounds may indicate different heart disease types including cardiovascular diseases, cardiac murmurs and other types of cardiovascular diseases due to extra heart sounds. The heart sounds may be analyzed through digitally recorded heart sound signals, using various techniques present in the art to detect and identify abnormal heart sounds. This helps us to check whether a subject to be monitored having healthy or unhealthy heart conditions. Artificial intelligence (AI) based abnormal heart sounds detection models are more promising in the present research field. The Artificial intelligence (AI) based abnormal heart sounds detection models with supervised learning requires a substantial amount of different training datasets covering all different heart disease types for the training. However, obtaining the different training datasets accurately is quite challenging as the heart sound signals are highly susceptible to background noise.

SUMMARY

Embodiments of the present disclosure present technological improvements as solutions to one or more of the above-mentioned technical problems recognized by the inventors in conventional systems.

In an aspect, there is provided a processor-implemented method comprising the steps of: receiving, via one or more hardware processors, a plurality of normal heart sound signals, from an input data source, wherein each normal heart sound signal of the plurality of normal heart sound signals is of a predefined time window, and indicative of normal heart condition; pre-processing, via the one or more hardware processors, each normal heart sound signal, to obtain a plurality of normal spectrograms for the plurality of normal heart sound signals, wherein each normal spectrogram of the plurality of normal spectrograms comprises spectrographic properties associated with the normal heart sound signal; and generating, via the one or more hardware processors, a semi-supervised learning model trained with training data, wherein the training data comprises probability distribution of the spectrographic properties of each normal spectrogram of the plurality of normal spectrograms, and wherein the semi-supervised learning model is generated by: transforming each normal spectrogram into a vector representation, to obtain a plurality of normal input vectors for the plurality of normal spectrograms; determining a normal latent vector for each normal input vector, to obtain a plurality of normal latent vectors for the plurality of normal input vectors, using an encoder unit of the semi-supervised learning model, wherein each normal latent vector comprises a latent representation of the associated normal input vector in a predefined reduced dimension; determining a normal reconstructed vector for each normal latent vector to obtain a plurality of normal reconstructed vectors for the plurality of normal latent vectors, using a decoder unit of the semi-supervised learning model, wherein each normal reconstructed vector among the plurality of normal reconstructed vectors comprises a reconstructed vector representation of the associated normal input vector; and minimizing an optimization function of the semi-supervised learning model by estimating a set of weights for each normal reconstructed vector of the plurality of normal reconstructed vectors, to obtain a minimized optimization function, wherein the optimization function is defined based on (i) a logarithmic cross entropy of the corresponding normal input vector and the corresponding normal reconstructed vector and (ii) a Kullback-Leibler (KL) divergence between the probability distribution of the corresponding normal latent vector, and a predefined Gaussian distribution with a predefined set of parameters comprising a predefined mean vector and a predefined variance vector.

In another aspect, there is provided a system comprising: a memory storing instructions; one or more Input/Output (I/O) interfaces; and one or more hardware processors coupled to the memory via the one or more I/O interfaces, wherein the one or more hardware processors are configured by the instructions to: receive a plurality of normal heart sound signals, from an input data source, wherein each normal heart sound signal of the plurality of normal heart sound signals is of a predefined time window, and indicative of normal heart condition; pre-process each normal heart sound signal, to obtain a plurality of normal spectrograms for the plurality of normal heart sound signals, wherein each normal spectrogram of the plurality of normal spectrograms comprises spectrographic properties associated with the normal heart sound signal; and generate a semi-supervised learning model trained with training data, wherein the training data comprises probability distribution of the spectrographic properties of each normal spectrogram of the plurality of normal spectrograms, and wherein the semi-supervised learning model is generated by: transforming each normal spectrogram into a vector representation, to obtain a plurality of normal input vectors for the plurality of normal spectrograms; determining a normal latent vector for each normal input vector, to obtain a plurality of normal latent vectors for the plurality of normal input vectors, using an encoder unit of the semi-supervised learning model, wherein each normal latent vector comprises a latent representation of the associated normal input vector in a predefined reduced dimension; determining a normal reconstructed vector for each normal latent vector to obtain a plurality of normal reconstructed vectors for the plurality of normal latent vectors, using a decoder unit of the semi-supervised learning model, wherein each normal reconstructed vector among the plurality of normal reconstructed vectors comprises a reconstructed vector representation of the associated normal input vector; and minimizing an optimization function of the semi-supervised learning model by estimating a set of weights for each normal reconstructed vector of the plurality of normal reconstructed vectors, to obtain a minimized optimization function, wherein the optimization function is defined based on (i) a logarithmic cross entropy of the corresponding normal input vector and the corresponding normal reconstructed vector and (ii) a Kullback-Leibler (KL) divergence between the probability distribution of the corresponding normal latent vector, and a predefined Gaussian distribution with a predefined set of parameters comprising a predefined mean vector and a predefined variance vector.

In yet another aspect, there is provided a computer program product comprising a non-transitory computer readable medium having a computer readable program embodied therein, wherein the computer readable program, when executed on a computing device, causes the computing device to: receive a plurality of normal heart sound signals, from an input data source, wherein each normal heart sound signal of the plurality of normal heart sound signals is of a predefined time window, and indicative of normal heart condition; pre-process each normal heart sound signal, to obtain a plurality of normal spectrograms for the plurality of normal heart sound signals, wherein each normal spectrogram of the plurality of normal spectrograms comprises spectrographic properties associated with the normal heart sound signal; and generate a semi-supervised learning model trained with training data, wherein the training data comprises probability distribution of the spectrographic properties of each normal spectrogram of the plurality of normal spectrograms, and wherein the semi-supervised learning model is generated by: transforming each normal spectrogram into a vector representation, to obtain a plurality of normal input vectors for the plurality of normal spectrograms; determining a normal latent vector for each normal input vector, to obtain a plurality of normal latent vectors for the plurality of normal input vectors, using an encoder unit of the semi-supervised learning model, wherein each normal latent vector comprises a latent representation of the associated normal input vector in a predefined reduced dimension; determining a normal reconstructed vector for each normal latent vector to obtain a plurality of normal reconstructed vectors for the plurality of normal latent vectors, using a decoder unit of the semi-supervised learning model, wherein each normal reconstructed vector among the plurality of normal reconstructed vectors comprises a reconstructed vector representation of the associated normal input vector; and minimizing an optimization function of the semi-supervised learning model by estimating a set of weights for each normal reconstructed vector of the plurality of normal reconstructed vectors, to obtain a minimized optimization function, wherein the optimization function is defined based on (i) a logarithmic cross entropy of the corresponding normal input vector and the corresponding normal reconstructed vector and (ii) a Kullback-Leibler (KL) divergence between the probability distribution of the corresponding normal latent vector, and a predefined Gaussian distribution with a predefined set of parameters comprising a predefined mean vector and a predefined variance vector.

It is to be understood that both the foregoing general description and the following detailed description are exemplary and explanatory only and are not restrictive of the embodiments of the present disclosure, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION OF EMBODIMENTS

Figure 1:
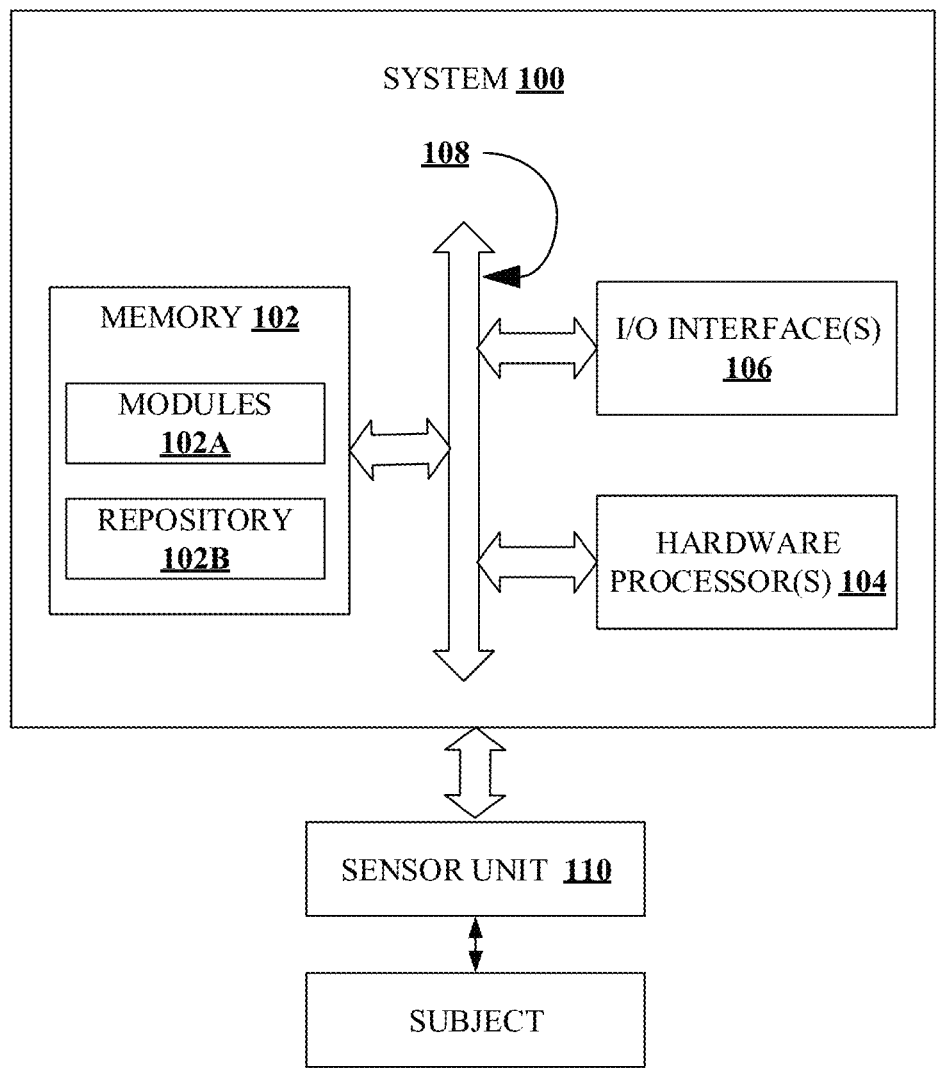
FIG. 1 is an exemplary block diagram of a system for identifying presence of abnormal heart sounds of a subject being monitored, in accordance with some embodiments of the present disclosure.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

Analysis of heart sounds using a stethoscope is a basic medical technique that has been widely carried out by physicians to check heart functioning of a subject. In the context of the present disclosure, the expression 'subject' refers to a living being such as a human being or an animal. Normal heart sounds generated by a healthy heart during closing and opening of heart valves is distinguishably different than abnormal heart sounds generated by an unhealthy heart. With advancement in the technology, digital heart sound signals may be analyzed to identify the abnormal heart sounds. Further, the abnormal heart sounds may have diverse frequency characteristics which helps to identify different heart disease types including cardiovascular diseases, cardiac murmurs, diseases due to extra heart sounds, and so on.

Detection of such abnormal heart sounds from digital heart sound signals is broadly classified into (i) segregation based models and (ii) non-segregation based models. The segregation based models may segregate fundamental heart sounds from the digital heart sound time-series signals for analysis. Morphological features in time, frequency and time-frequency domains are derived from the segregated heart sounds for detecting the abnormal heart sounds. However, the heart sound signals are highly susceptible to background noise and hence the segregation of the fundamental heart sounds is technically challenging and may yield inaccurate detection of the abnormal heart sounds. The non-segregation models may also yield inaccurate detection of the abnormal heart sounds, as these models may analyze entire heart sound time-series signals without segregation of the fundamental heart sounds.

Automatic detection of the abnormal heart sounds from digital heart sound signals using artificial intelligence (AI) is an important area in medicine for low-cost screening. Artificial intelligence (AI) based abnormal heart sounds detection models require a training data for learning before their generation, where the training data can be obtained through the segregation based models and the non-segregation based models. However, the Artificial intelligence (AI) based abnormal heart sounds detection models with supervised learning requires a substantial amount of different training datasets covering all heart disease types for the training. If the training datasets is not accurate, then generating an efficient Artificial intelligence (AI) based abnormal heart sounds detection models with supervised learning is quite challenging.

The present disclosure herein provide methods and systems that solves the technical problem of identifying presence of the abnormal heart sounds of the subject using an efficient semi-supervised learning model. The semi-supervised learning model is generated based on probability distribution of spectrographic properties obtained from heart sound signals of healthy subjects. A Kullback-Leibler (KL) divergence between a predefined Gaussian distribution and an encoded probability distribution of the semi-supervised learning model is determined as an anomaly score for identifying the abnormal heart sounds. The semi-supervised learning model is generated without any training data related to the heart disease types for the training.

Referring now to the drawings, and more particularly to FIG. 1 through FIG. 5B, where similar reference characters denote corresponding features consistently throughout the figures, there are shown preferred embodiments and these embodiments are described in the context of the following exemplary systems and/or methods.

FIG. 1 is an exemplary block diagram of a system 100 for identifying presence of abnormal heart sounds of a subject being monitored, in accordance with some embodiments of the present disclosure. In an embodiment, the system 100 includes or is otherwise in communication with one or more hardware processors 104, communication interface device(s) or input/output (I/O) interface(s) 106, and one or more data storage devices or memory 102 operatively coupled to the one or more hardware processors 104. The one or more hardware processors 104, the memory 102, and the I/O interface(s) 106 may be coupled to a system bus 108 or a similar mechanism.

The I/O interface(s) 106 may include a variety of software and hardware interfaces, for example, a web interface, a graphical user interface, and the like. The I/O interface(s) 106 may include a variety of software and hardware interfaces, for example, interfaces for peripheral device(s), such as a keyboard, a mouse, an external memory, a plurality of sensor devices, a printer and the like. Further, the I/O interface(s) 106 may enable the system 100 to communicate with other devices, such as web servers and external databases.

The I/O interface(s) 106 can facilitate multiple communications within a wide variety of networks and protocol types, including wired networks, for example, local area network (LAN), cable, etc., and wireless networks, such as Wireless LAN (WLAN), cellular, or satellite. For the purpose, the I/O interface(s) 106 may include one or more ports for connecting a number of computing systems with one another or to another server computer. Further, the I/O interface(s) 106 may include one or more ports for connecting a number of devices to one another or to another server.

The one or more hardware processors 104 may be implemented as one or more microprocessors, microcomputers, microcontrollers, digital signal processors, central processing units, state machines, logic circuitries, and/or any devices that manipulate signals based on operational instructions. Among other capabilities, the one or more hardware processors 104 are configured to fetch and execute computer-readable instructions stored in the memory 102. In the context of the present disclosure, the expressions 'processors' and 'hardware processors' may be used interchangeably. In an embodiment, the system 100 can be implemented in a variety of computing systems, such as laptop computers, portable computer, notebooks, hand-held devices, workstations, mainframe computers, servers, a network cloud and the like.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, the memory 102 includes a plurality of modules 102A and a repository 102B for storing data processed, received, and generated by one or more of the plurality of modules 102A. The plurality of modules 102A may include routines, programs, objects, components, data structures, and so on, which perform particular tasks or implement particular abstract data types.

The plurality of modules 102A may include programs or computer-readable instructions or coded instructions that supplement applications or functions performed by the system 100. The plurality of modules 102A may also be used as, signal processor(s), state machine(s), logic circuitries, and/or any other device or component that manipulates signals based on operational instructions. Further, the plurality of modules 102A can be used by hardware, by computer-readable instructions executed by the one or more hardware processors 104, or by a combination thereof. In an embodiment, the plurality of modules 102A can include various sub-modules (not shown in FIG. 1). Further, the memory 102 may include information pertaining to input(s)/output(s) of each step performed by the processor(s) 104 of the system 100 and methods of the present disclosure.

The repository 102B may include a database or a data engine. Further, the repository 102B amongst other things, may serve as a database or includes a plurality of databases for storing the data that is processed, received, or generated as a result of the execution of the plurality of modules 102A. Although the repository 102B is shown internal to the system 100, it will be noted that, in alternate embodiments, the repository 102B can also be implemented external to the system 100, where the repository 102B may be stored within an external database (not shown in FIG. 1) communicatively coupled to the system 100. The data contained within such external database may be periodically updated. For example, new data may be added into the external database and/or existing data may be modified and/or non-useful data may be deleted from the external database. In one example, the data may be stored in an external system, such as a Lightweight Directory Access Protocol (LDAP) directory and a Relational Database Management System (RDBMS). In another embodiment, the data stored in the repository 102B may be distributed between the system 100 and the external database.

In an embodiment, the system 100 is connected to a sensor unit 110. The sensor unit 110 is configured to receive digitalized heart sound signals from the subject being monitored. In an embodiment, the sensor unit 110 may be a phonocardiogram (PCG) sensor or any other sensor that may capable of acquiring the digitalized heart sound signals from the subject being monitored. In an embodiment, the sensor unit 110 may be integral part of the system 100 or may be externally connected to the system 100 through the I/O interface(s) 106 either wirelessly or with a wired connection.

Figure 2A:
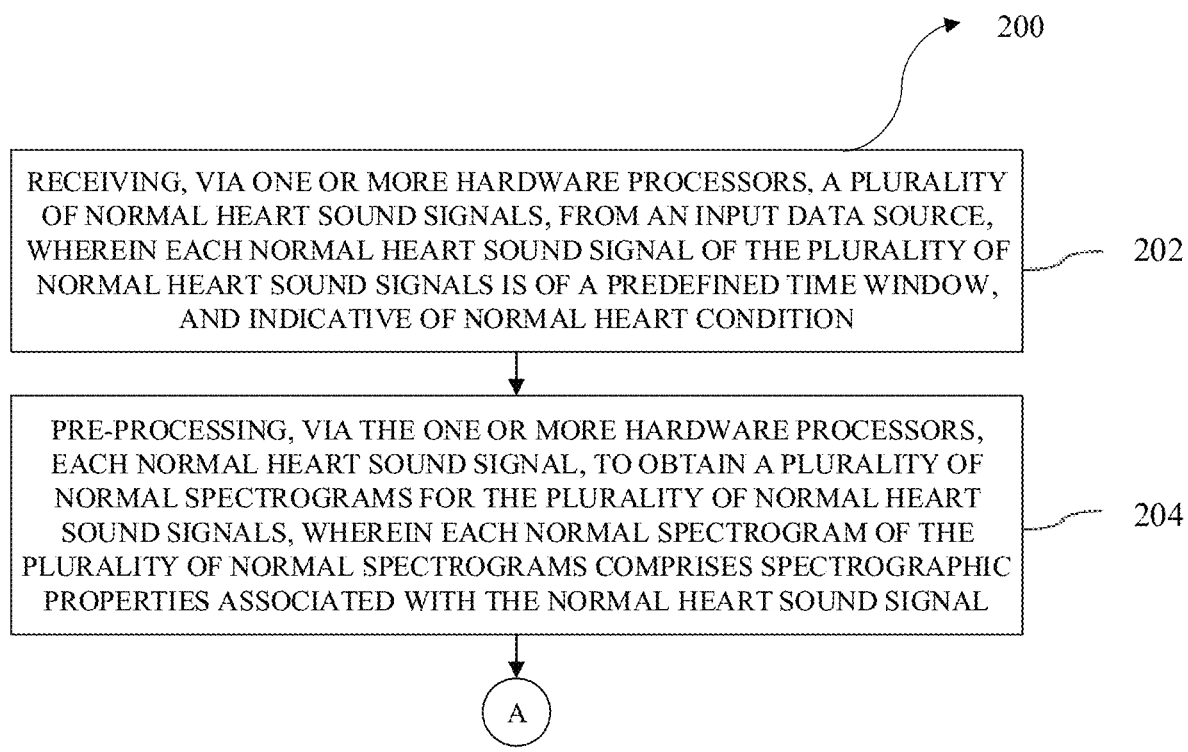
FIG. 2A through FIG. 2C illustrate exemplary flow diagrams of a processor-implemented method for identifying presence of the abnormal heart sounds of the subject being monitored, in accordance with some embodiments of the present disclosure.
Figure 2B:
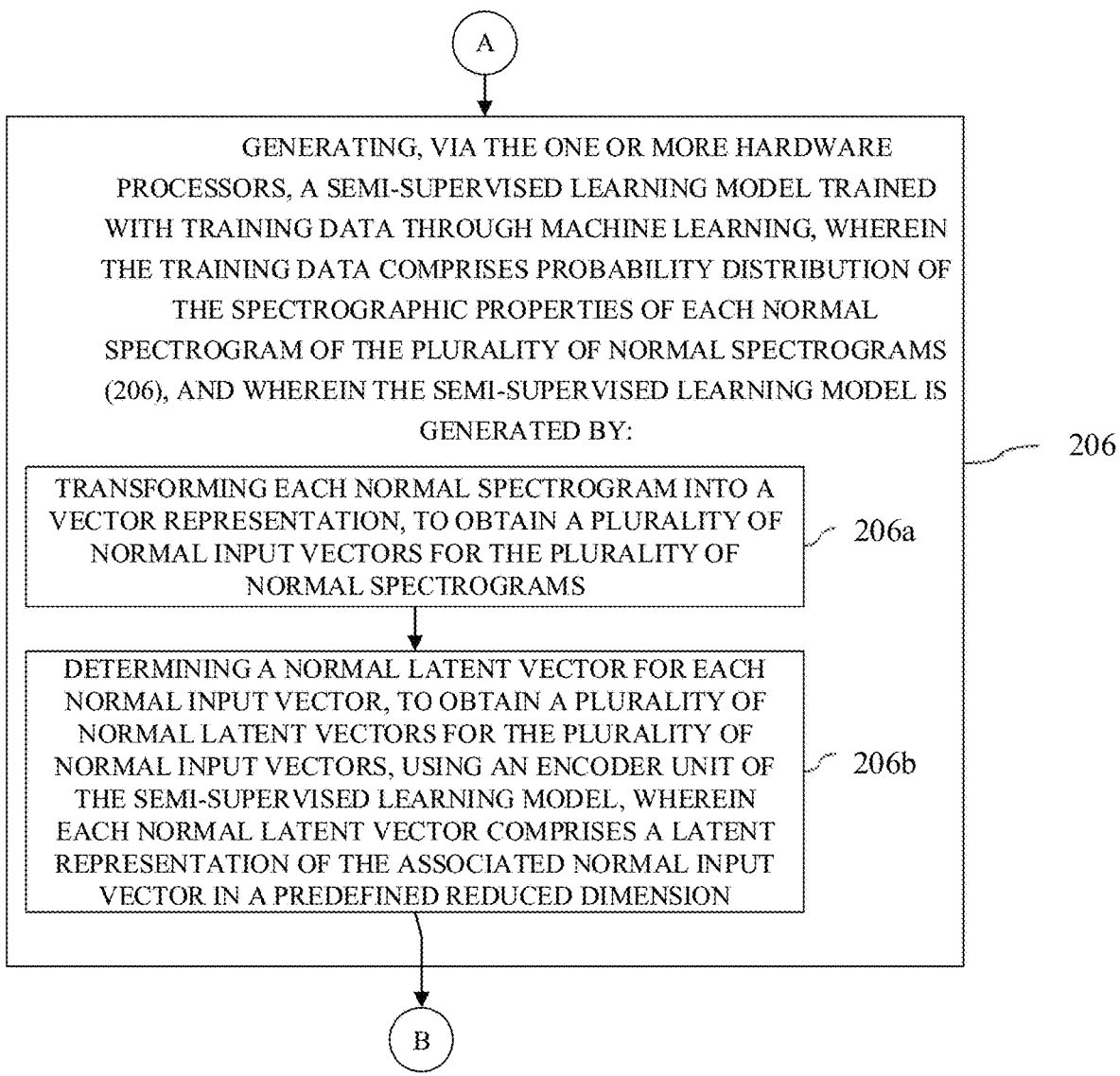
Figure 2C:
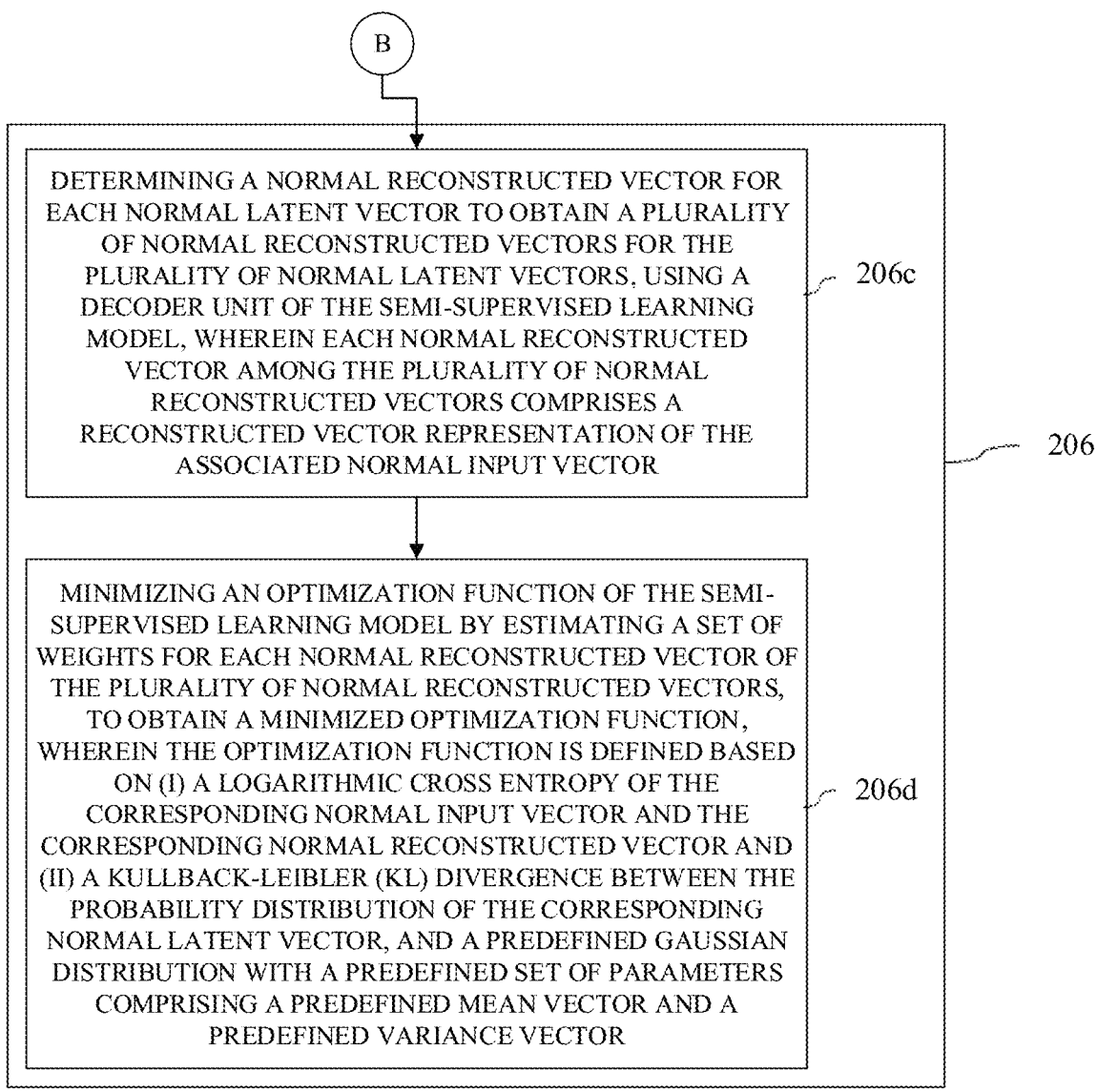

Referring to FIG. 2A through FIG. 2C, components and functionalities of the system 100 are described in accordance with an example embodiment of the present disclosure. FIG. 2A through FIG. 2C illustrate exemplary flow diagrams of a processor-implemented method 200 for identifying presence of abnormal heart sounds of the subject being monitored, in accordance with some embodiments of the present disclosure. Although steps of the method 200 including process steps, method steps, techniques or the like may be described in a sequential order, such processes, methods and techniques may be configured to work in alternate orders. In other words, any sequence or order of steps that may be described does not necessarily indicate a requirement that the steps be performed in that order. The steps of processes described herein may be performed in any practical order. Further, some steps may be performed simultaneously, or some steps may be performed alone or independently.

At step 202 of the method 200, the one or more hardware processors 104 of the system 100 are configured to receive a plurality of normal heart sound signals, from an input data source. The plurality of normal heart sounds signal is of healthy subjects having normal heart conditions. Each normal heart sound signal among the plurality of normal heart sound signals is of a prolonged duration. However, the normal heart sound signal with a predefined time window is considered at a time for analysis. In an embodiment, the predefined time window may be for example, 10 sec. From available scientific knowledge, the heart sound signal of 10 seconds duration may be enough for analysis, as it may have 8 to 16 complete cardiac cycles (including systolic phase and diastolic phase) depending on heart rate ranging from 50 to 100 beats per second (bpm). In an embodiment, the input data source may be stored in the repository 102B of the system 100. In an embodiment, the input data source may be one of the publicly available dataset having the heart sound signals of the healthy subjects. In an embodiment, the input data source may include a combination of one or more publicly available datasets having the heart sound signals of the healthy subjects.

Figure 4A:
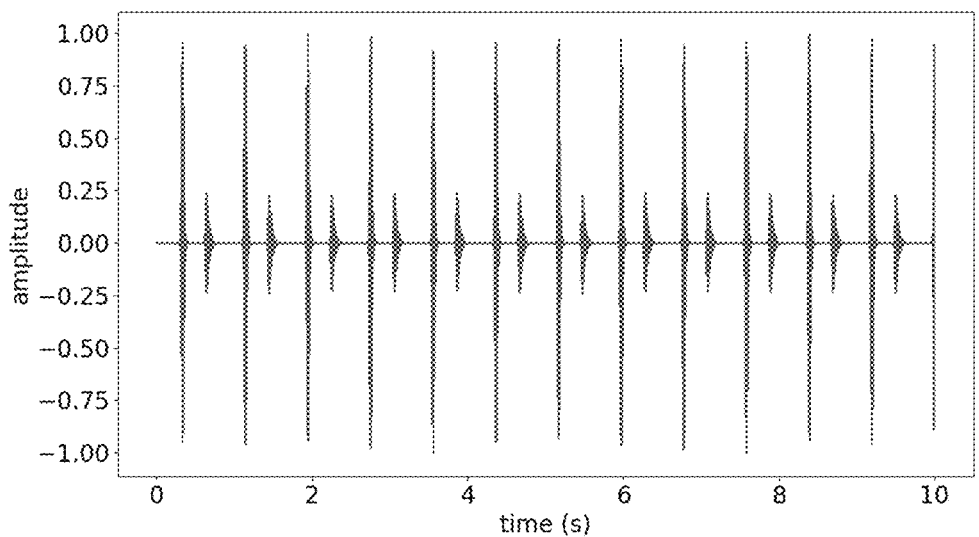
FIG. 4A and FIG. 4B illustrate graphs showing a sample normal heart sound signal and a normal spectrogram of the sample normal heart sound signal, respectively, in accordance with some embodiments of the present disclosure.
Figure 4B:
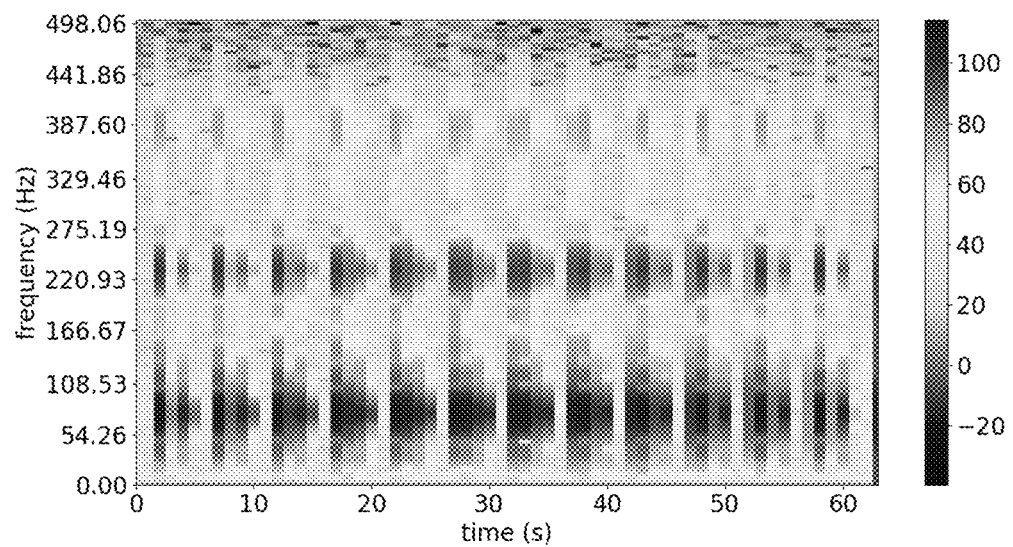

At step 204 of the method 200, the one or more hardware processors 104 of the system 100 are configured to pre-process each normal heart sound signal obtained at step 202 of the method 200, to obtain a normal spectrogram. A plurality of normal spectrograms is obtained after pre-processing the plurality of normal heart sound signals. Each normal spectrogram includes spectrographic properties associated with the corresponding normal heart sound signal. In an embodiment, each normal heart sound signal is filtered using a low-pass filter with a predefined cut-off frequency to obtain a filtered normal heart sound signal. In an embodiment, the predefined cut-off frequency may be for example, 500 Hz. Then, a down sampling at a predefined down-sampling frequency is performed, on each filtered normal heart sound signal, to obtain a down-sampled normal heart sound signal. In an embodiment, the predefined down-sampling frequency may be for example, 1000 Hz. Further, each down-sampled normal heart sound signal is transformed using a Short-time Fourier Transform (STFT) technique with a tukey window of length 256 ms long and 38% overlapping, to obtain the normal spectrogram for the corresponding normal heart sound signal. Each normal spectrogram includes a resolution of 64 time bins and 129 frequency bins. A first frequency bin is discarded to obtain a resolution of 64×128λ1. Then each normal spectrogram is normalized between 0 and 1 using a min-max normalization. FIG. 4A and FIG. 4B illustrate graphs showing a sample normal heart sound signal and a normal spectrogram of the sample normal heart sound signal, respectively, in accordance with some embodiments of the present disclosure. The normal spectrogram shown in FIG. 4B shows the graph including the spectrographic properties of the sample normal heart sound signal shown in FIG. 4A.

In an embodiment, the low-pass filter may be a software filter or a hardware filter. If it is the software filter, then such filter may be present as one of the module of the plurality of modules 102A. If it is the hardware filter, then such filter may be integral part of the system 100, wherein the one or more hardware processors 104 may be configured to serve as the low-pass filter, or such filter may be external to the system 100, may be connected or communicated with the system 100 either wirelessly or with the wired connection, through the I/O interface(s) 106.

At step 206 of the method 200, the one or more hardware processors 104 of the system 100 are configured to generate a semi-supervised learning model that is trained with training data. The semi-supervised learning model may be trained and learned the training data through machine learning. The training data includes probability distribution of the spectrographic properties of each normal spectrogram of the plurality of normal spectrograms obtained at step 204 of the method 200.

Figure 3A:
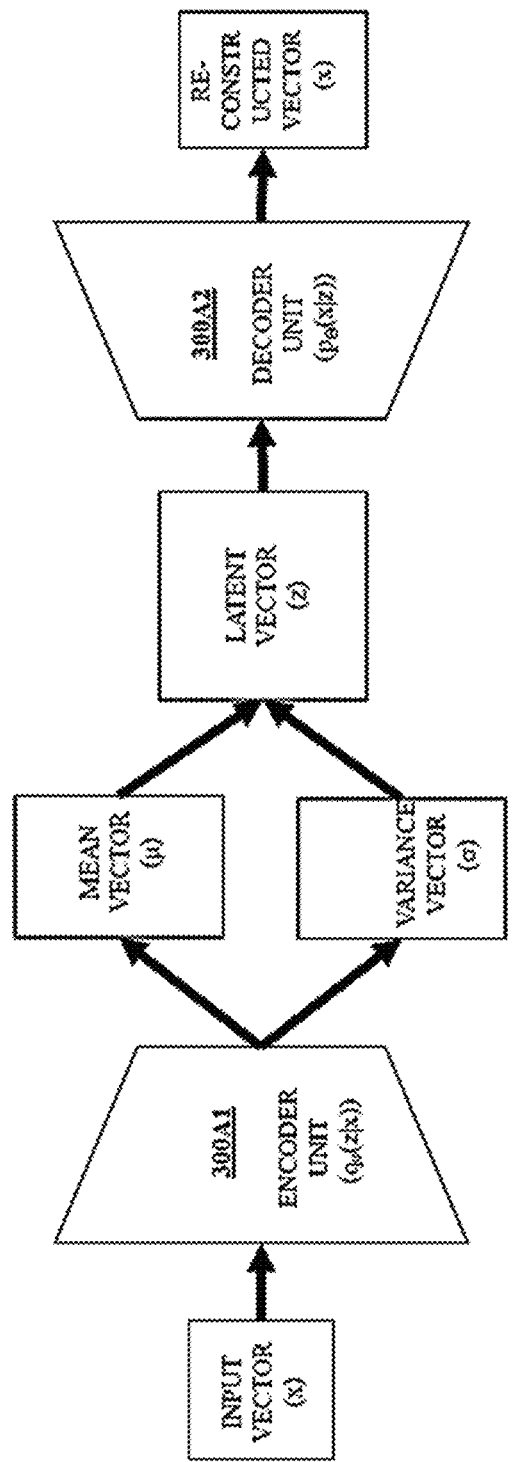
FIG. 3A is a schematic block diagram illustrating an architecture of a semi-supervised learning model for identifying presence of the abnormal heart sounds of the subject being monitored, in accordance with some embodiments of the present disclosure.

The semi-supervised learning model is a convolutional variational autoencoder. In an embodiment, the convolutional variational autoencoder comprises an encoder unit and a decoder unit. FIG. 3A is a schematic block diagram illustrating an architecture of a semi-supervised learning model 300A for identifying the presence of the abnormal heart sounds of the subject being monitored, in accordance with some embodiments of the present disclosure. The encoder unit 300A1 extracts features from vector representation of heart sound signal. A set of weights in a form of a mean vector and a variance vector are assigned to subsequently generates a latent vector. The extracted features are of indicative of the probability distribution of the spectrographic properties of each normal heart sound signal of the plurality of normal heart sound signals. The latent vector includes a latent representation of the probability distribution of the spectrographic properties of each heart sound signal, with a reduced dimension. The decoder unit 300A2 reconstructs the latent representation to the original space by generating a reconstructed vector. A difference between the latent vector representation of heart sound signal and its corresponding reconstructed representation is called the reconstruction loss.

The encoder unit 300A1 is a 2-dimensional (2-D) convolutional neural network (CNN) structure including a total of 3 convolutional neural network (CNN) layers. Each CNN layer of the encoder unit 300A1 is associated with a batch normalization layer and a max-pooling layer. Each CNN layer of the encoder unit 300A1 includes a kernel size of 4×4. A pooling size of each max-pooling layer is taken as 2×2. Also, each CNN layer of the encoder unit 300A1 includes a total of 64 filters. An output of final max-pooling layer is flattened to generate the latent representation with a predefined reduced dimensionality. The decoder unit 300A2 is also the 2-dimensional (2-D) convolutional neural network (CNN) structure including a total of 4 convolutional neural network (CNN) layers. The structure of the decoder unit 300A2 is inverse to the structure of the encoder unit 300A1, except the last CNN layer. However, the max-pooling layers are replaced by up-sampling layers of same size as that of max-pooling layers, to gradually enhance the predefined reduced dimensionality of latent representation to the original space. The output of the final up-sampling layer is applied to the last CNN layer (forth CNN layer) which includes a single filter to reconstruct the latent representation to the original space. A Rectified Linear Unit (ReLU) is used as a non-linear activation function in all the convolutional layers of the convolutional variational autoencoder 300A except the last CNN layer of the decoder unit 300A2. In an embodiment, the last CNN layer of the decoder unit 300A2 takes a sigmoid activation function.

Figure 3B:
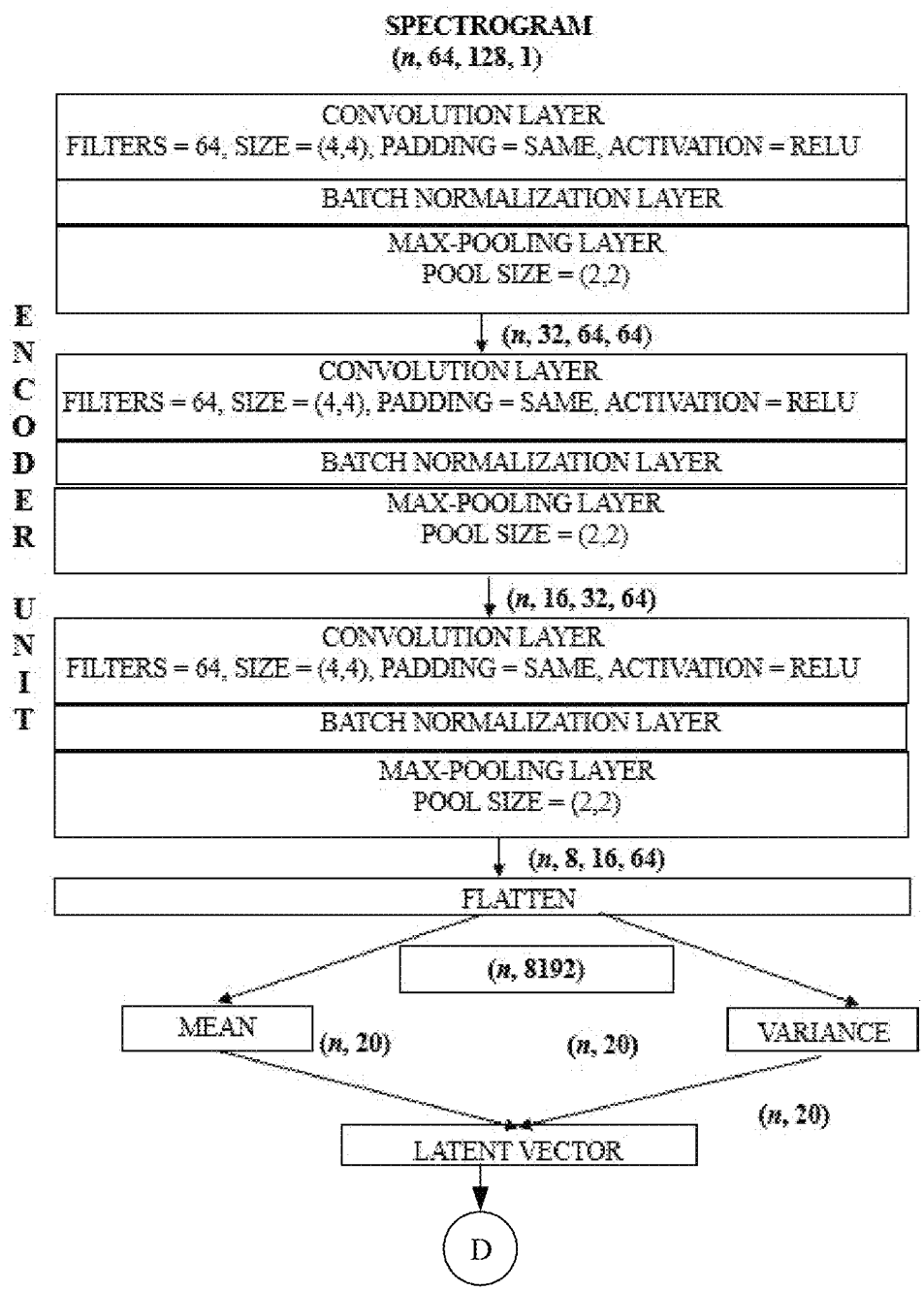
FIG. 3B and FIG. 3C illustrate functional flow diagrams of the semi-supervised learning model for identifying presence of the abnormal heart sounds of the subject being monitored, in accordance with some embodiments of the present disclosure.
Figure 3C:
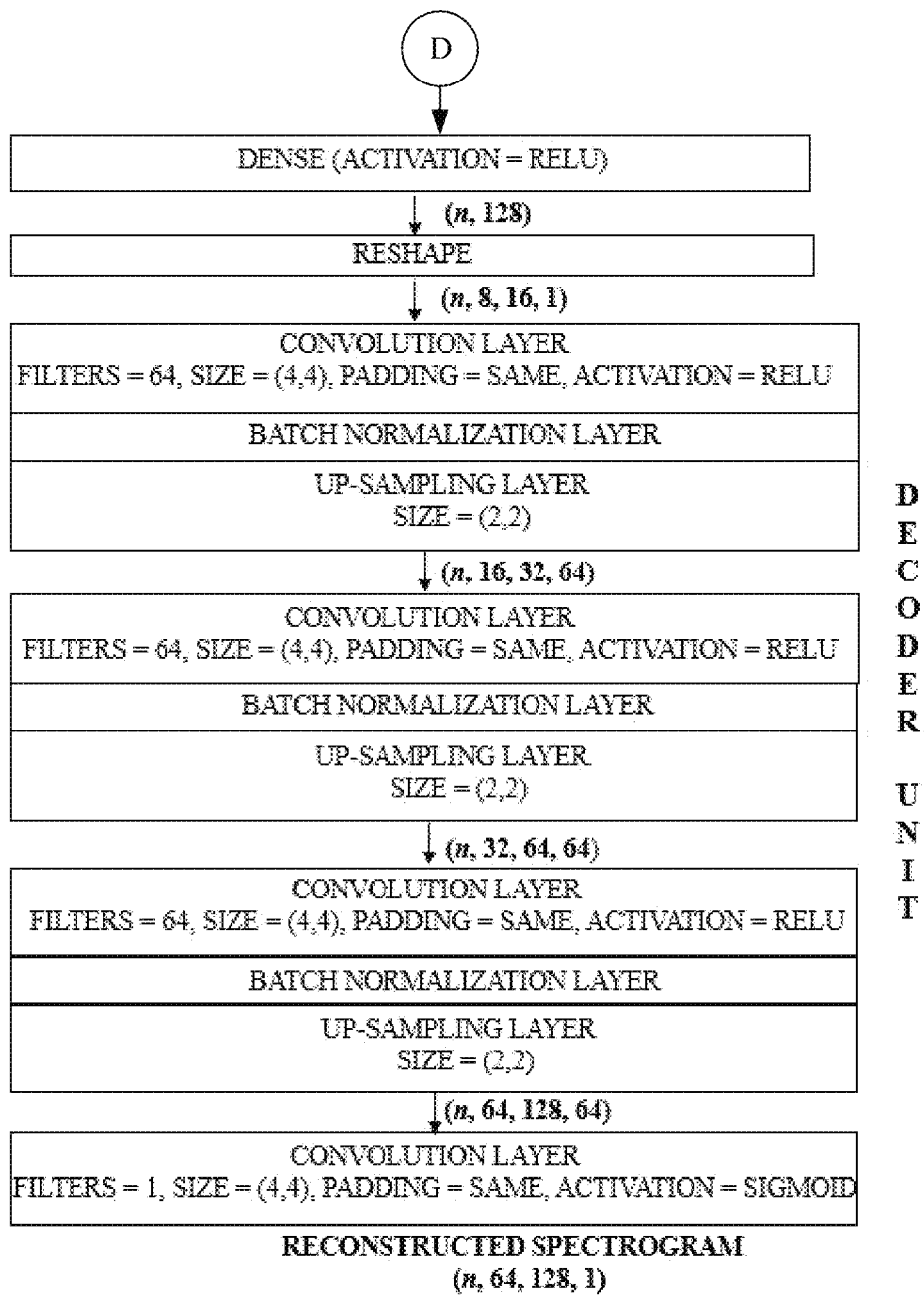

FIG. 3B and FIG. 3C illustrate functional flow diagrams of the semi-supervised learning model for identifying presence of the abnormal heart sounds of the subject being monitored, in accordance with some embodiments of the present disclosure. Firstly, at step 206a of the method 200, each normal spectrogram obtained at step 204 of the method 200, is transformed into a vector representation, to obtain a normal input vector for the corresponding normal spectrogram. Hence a plurality of normal input vectors is obtained from the plurality of normal spectrograms. Each normal input vector among the plurality of normal input vectors is given at a time, to the encoder unit 300A1 of the semi-supervised learning model 300A. A sample size (N) of the plurality of normal input vectors is predefined before giving them to the encoder unit 300A1. In an embodiment, the predefined sample size (N) may be 1000 samples of normal input vectors. As shown in FIG. 3B, the normal input vector with the dimension (n, 64, 128, 1) is given to the first CNN layer of the encoder unit 300A. Here n denotes a sample number of the sample size, where n=1,2, 3, . . . , N. Also, here (64, 128,1) of the (n, 64,128, 1) denotes time bins and frequency bins in 3-dimensional representation and defines the dimension of the normal input vector. The dimension of the normal input vector indicates spectrographic properties of the corresponding normal heart sound signal. The encoder unit learns the probability distribution from the spectrographic properties associated with each normal input vector.

At step 206b of the method 200, the 3 CNN layers of the encoder unit 300A1 extracts the features of the normal input vector and determine a normal latent vector for each normal input vector. Hence, the encoder unit 300A1 determines a plurality of normal latent vectors for the plurality of normal input vectors. Each normal latent vector comprises the latent representation of the associated normal input vector in the predefined reduced dimension. In an embodiment, the predefined reduced dimension is heuristically selected as 20. In FIG. 3B, the dimension of the normal latent vector is shown as 20 (n, 20).

The encoder unit 300A1 of the semi-supervised learning model 300A transforms feature space x (spectrographic features) of the normal input vector into a gaussian probability distribution and allowing random sampling from the gaussian probability distribution to generate the normal latent vector z. A predefined set of weights including a predefined mean vector (μ) and a predefined variance vector (a) are assigned to the random sampling before generating the normal latent vector z. In an embodiment, during at initialization stage of the encoder unit 300A1, the predefined mean vector (p) is zero and the predefined variance vector (a) is a unit variance vector. Later, the predefined variance vector is calculated based on number of input neurons and output neurons present in the corresponding CNN layer of the encoder unit 300A1.

At step 206c of the method 200, the decoder unit 300A2 of the semi-supervised learning model 300A transforms the latent space to the original feature space x of the normal input vector. The normal latent vector z with the dimension (n,20) determined by the encoder unit 300A1 is being input to the decoder unit 300A1 as shown in FIG. 3C. The CNN layers of the decoder unit try to re-constructs the original space having the original dimensions from the latent space. A normal reconstructed vector for each normal latent vector (z) is determined by the decoder unit 300A2. Hence, a plurality of normal reconstructed vectors for the plurality of normal latent vectors are determined in this step. The original space re-constructed by the decoder unit 300A2 through the normal reconstructed vector is to same as the original feature space x of the normal input vector.

An optimization function p(x) defined as a probability of determining the normal reconstructed vector from the corresponding normal input vector via the corresponding normal latent vector (z). In other words, the optimization function p(x) is defined based on (i) a logarithmic cross entropy of the corresponding normal input vector and the corresponding normal reconstructed vector and (ii) a Kullback-Leibler (KL) divergence between the probability distribution of the corresponding normal latent vector, and a predefined Gaussian distribution with the predefined set of weights. An objective of the semi-supervised learning model 200A is to maximize a marginal likelihood of the optimization function p(x) to observe x, where, $$p(x) = \int p_\theta(x|z) p_\theta(z) dz \quad (1)$$

where, $p_\theta(x|z)$ denotes a probability of getting the normal reconstructed vector from the corresponding normal latent vector (z), $p_\theta(z)$ denotes a predefined Gaussian distribution at the latent space, and θ is a weight of the decoder unit 300A2 that represents the normal reconstructed vector.

The optimization function p(x) can also be defined as equivalent to maximizing Evidence Lower Bound (ELBO) (L) which is solved by minimizing the negative ELBO as a loss function mentioned below:

$$L = L_L - L_{KL} \quad (2)=$$

$$= E_{q_\phi(Z|X)}[ln(P\theta(X|Z))] D_{KL}[q\phi(Z|X)\|P_\theta(z)] \quad (3)=$$

$$\ln(p(x)) - D_{KL}[q\phi(Z|X)\|P\theta(Z)] \quad (4)$$

where, $q_\phi(z|x)$ denotes an approximate posterior distribution of the normal latent vector (z), $D_{KL}[q_\phi(Z|X)\|p_\theta(z)]$ denotes a measurement of a Kullback-Leibler (KL) divergence between the approximate posterior distribution and the predefined Gaussian distribution at the latent space, and represents a weight of the encoder unit 300A1. The first term '$E_{q_\phi(z|x)}[\ln(p\theta(x|z))]$' present in equation (3) indicates the re-construction of original space x from the approximate posterior distribution $q_\phi(z|x)$ and the likelihood of $p_\theta(x|z)$. The second term '$D_{KL}[q_\phi(z|x)\| P\theta(z)]$' present in equation (3) forces the approximate posterior distribution to be similar to the predefined Gaussian distribution at the latent space. Since the KL divergence is non-negative, L≤ln(p(x)) from equation (4) is computationally intractable.

At step 206d of the method 200, during the training of the semi-supervised learning model 300A, the weight ($\phi$) of the encoder unit 300A1 and the weight ($\theta$) of the decoder unit 300A2 (termed as a set of weights ($\phi$, $\theta$) of the semi-supervised learning model 300A from now on), are to be estimated for each normal input vector of the plurality of normal input vectors, such that the optimization function is minimum for the corresponding normal input vector. During the training, in order to apply backpropagation for learning the set of weights ($\phi$, $\theta$) of the semi-supervised learning model 300A, an expectation term is approximated by a finite number of samples from $q_\phi(z|x)$. Since both the predefined Gaussian distribution at the latent space $p_\theta(z)$ and the approximate posterior distribution of the normal latent vector (z) $q_\theta(z|x)$ are the gaussian distributions a below mentioned equation for the Kullback-Leibler (KL) divergence between the approximate posterior distribution $q\phi(z|x)$ and the predefined Gaussian distribution at the latent space $p_\theta(z)$, can be derived:

$$D_{KL}[q_\phi(z|x)\|P_\theta(z)] = -0.5\sum_{k=1}^{K}\left(1 + \ln\sigma_k^2 - \mu_k^2 - \sigma_k^2\right) \quad (5)$$

where K is the dimension of the normal latent vector (in this case it is 20), $\sigma_k$ and $\mu_k$ are $k^{th}$ component of the mean vector (v) and the variance vector ($\sigma$) of the approximate posterior distribution of the normal latent vector (z) $q\phi(z|x)$.

While training the semi-supervised learning model 300A, an amount of 40% dropout is applied to all the CNN layers of the encoder unit 300A1 and the decoder unit 300A2, to reduce chances of overfitting. An Adam optimizer with a learning rate of 0.001 with mini-batch size of 50 and 100 epochs is applied during the training to minimize the optimization function. A set of initial weights of neurons at each CNN layer are set using the Xavier initialization.

Once, the set of weights ($\phi$, $\theta$) of the semi-supervised learning model 300A for each normal input vector of the plurality of normal input vectors, are estimated, a set of average weights ($\phi_A$, $\theta_A$) are determined by taking an average of the respective weights. A minimized optimization function is obtained based on the optimization function and the set of average weights ($\phi_A$, $\theta_A$).

One the semi-supervised learning model 300A is generated after the training, the system 100 is ready for the testing phase to analyze the real-time heart sound signals. In an embodiment, the one or more hardware processors 104 of the system 100 are further configured to receive an input heart sound signal of the subject being monitored for identifying presence of abnormal heart sounds, using the sensor unit 110. In an embodiment, the input heart sounds signal is a continuous and an unobtrusive time-domain signal represented in seconds. The time window of the input heart sound signal is taken as the same as that of predefined time window of the plurality of normal heart sounds signal received at step 202 of the method 200, for further processing.

In an embodiment, the one or more hardware processors 104 of the system 100 are further configured to pre-process the input heart sound signal of the subject being monitored, to obtain an input spectrogram. The input spectrogram comprises the spectrographic properties of the input heart sound signal. In an embodiment, the input heart sound signal is filtered using the low-pass filter with the predefined cut-off frequency to obtain a filtered input heart sound signal. In an embodiment, the predefined cut-off frequency may be for example, 500 Hz. Then, the down sampling at the predefined down-sampling frequency is performed, on the filtered input heart sound signal, to obtain a down-sampled input heart sound signal. In an embodiment, the predefined down-sampling frequency may be for example, 1000 Hz. Further, the down-sampled input heart sound signal is transformed using the Short-time Fourier Transform (STFT) technique with the tukey window of length 256 ms long and 38% overlapping, to obtain the input spectrogram for the input heart sound signal. The input spectrogram includes the resolution of 64 time bins and 129 frequency bins. The first frequency bin is discarded to obtain the resolution of 64×128×1. Then the input spectrogram is normalized between 0 and 1 using the min-max normalization.

Figure 5A:
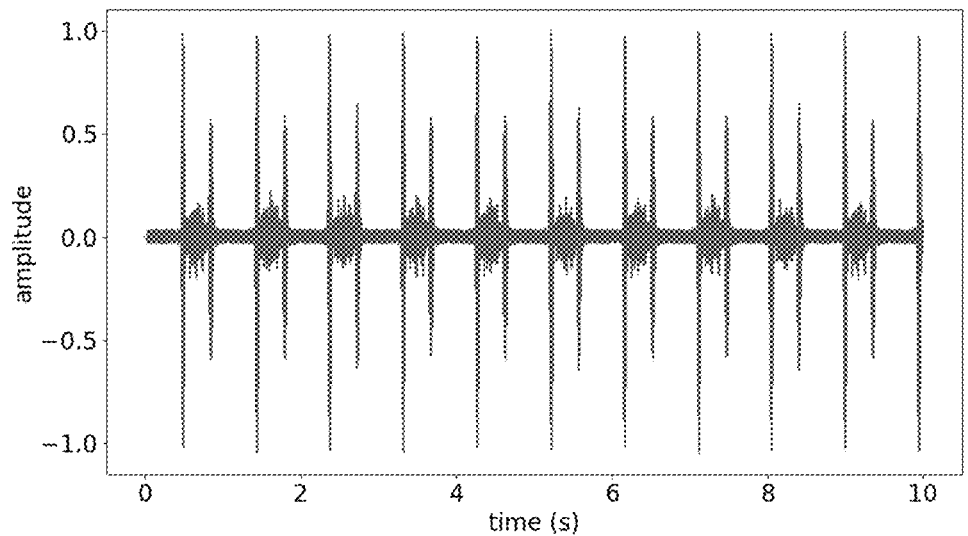
FIG. 5A and FIG. 5B illustrate graphs showing a sample abnormal heart sound signal and an abnormal spectrogram of the sample abnormal heart sound signal, respectively, in accordance with some embodiments of the present disclosure.
Figure 5B:
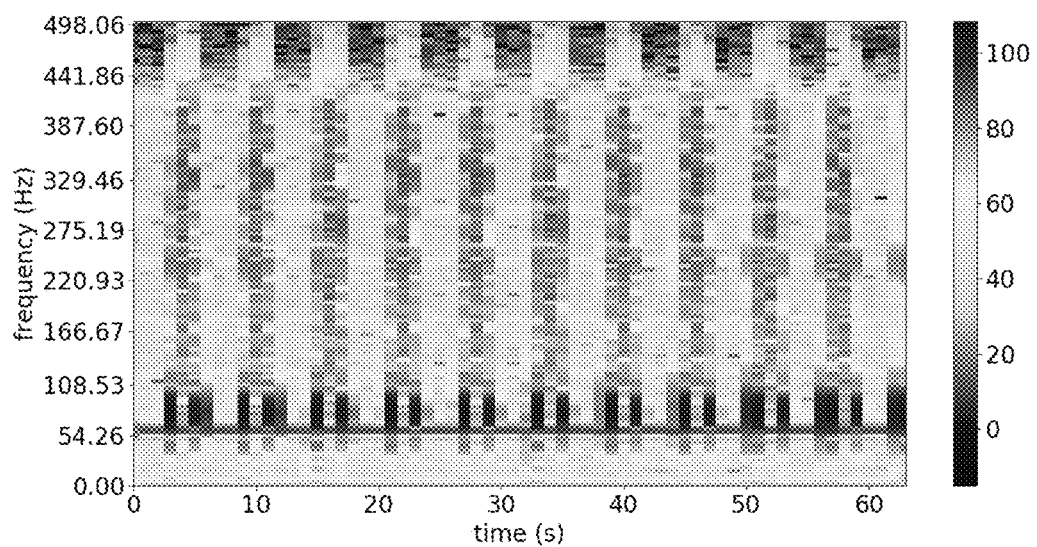

In an embodiment, the one or more hardware processors 104 of the system 100 are further configured to identify the presence of abnormal heart sounds of the subject being monitored, by analyzing the input spectrogram, using the semi-supervised learning model generated at step 206 of the method 200. FIG. 5A and FIG. 5B illustrate graphs showing a sample abnormal heart sound signal and an abnormal spectrogram of the sample abnormal heart sound signal, respectively, in accordance with some embodiments of the present disclosure. The obtained input spectrogram is transformed into the vector representation, to obtain an input vector. The obtained input vector is given to the encoder unit 300A1 of the semi-supervised learning model 300A generated at step 206 of the method 200. An input latent vector for the input vector is determined, using the encoder unit 300A1, wherein the input latent vector comprises the latent representation of the input vector.

A second set of parameters for the input latent vector, including the mean vector ($\mu$) and the variance vector ($\sigma$) are estimated, based on the minimized optimization function of the semi-supervised learning model 300A. The KL divergence between the approximate posterior distribution and the predefined Gaussian distribution at the latent space is determined using the equation (5). The determined KL divergence between the approximate posterior distribution and the predefined Gaussian distribution at the latent space, is measured as an anomaly score for identifying the presence of abnormal heart sounds of the subject being monitored. If the measured anomaly score is greater than a predefined anomaly threshold score, then this indicates a dissimilarity between the approximate posterior distribution and the predefined Gaussian distribution at the latent space, and hence detected as the presence of abnormal heart sounds. If the measured anomaly score is less than the predefined anomaly threshold score, then this indicates that both the approximate posterior distribution and the predefined Gaussian distribution at the latent space are similar and hence detected as absence of abnormal heart sounds.

Example Scenario:

A PhysioNet Challenge 2016 dataset including recordings of various annotated heart sound signals, is considered for training the semi-supervised learning model 300A. This is an annotated open access dataset including of 6 independent sets (set a through set f). Few of the recordings in each set are marked as noisy. Set b is excluded from the study as most of the recordings are noisy. The normal heart sound recordings in set a, set e and set f are used for the training. The abnormal heart sound recordings in the dataset are related to pathological conditions like coronary artery disease (CAD), valvular disease or aortic stenosis. The normal and abnormal heart sound recordings in set c and set d are used as validation data for tuning the weights of the semi-supervised learning model and heuristically determining the predefined anomaly threshold score. The predefined anomaly threshold score is determined from the following equation:

$$\text{Anomaly threshold score} = \text{normal}_{mean} + 1.5 \text{normal}_{std}$$

where $\text{normal}_{mean}$ and $\text{normal}_{std}$ are the mean and standard deviation of the anomaly scores of the normal heart sound recordings of set c and set d.

The final evaluation is done on two open access datasets and an in-house dataset, where the two open access datasets including (i) PASCAL heart sounds challenge dataset and (ii) University of Michigan heart sound and murmur library. Both these two open access datasets contain different types of heart diseases murmurs and extra heart sounds as abnormal recordings. The in-house dataset includes normal heart sound recordings and abnormal heart sound recordings measured by using a non-medical grade prototype digital stethoscope. A smaller (less than 10 seconds) and annotated noisy recordings are omitted from the two open access datasets and the remaining records are broken into the predefined time window (10 secs in this example) as mentioned at step 202 of the method 200. Each recording with the predefined time window is considered as an independent instance. Below table 1 indicates number of normal heart sound instances and abnormal heart sound instances in each dataset. The diseases corresponding to the abnormal heart sound recordings in the training and testing data are purposefully kept partially for a rigorous evaluation.

TABLE 1

| Dataset Name | Sampling rate | Normal heart sound instances | Abnormal heart sound instances |
| --- | --- | --- | --- |
| PhysioNet Set a | 2000 Hz | 339 | 782 |
| PhysioNet Set c | 2000 Hz | 24 | 102 |
| PhysioNet Set d | 2000 Hz | 18 | 33 |
| PhysioNet Set e | 2000 Hz | 3267 | 223 |
| PhysioNet Set f | 2000 Hz | 238 | 94 |
| PASCAL | 4000 Hz | 69 | 59 |
| University of Michigan | 44100 Hz | 12 | 135 |
| In-house dataset | 8000 Hz | 208 | 313 |

The semi-supervised learning model 300A is trained on an Intel The proposed network is trained on an Intel® Xeon(R) 16-core processor, having 64 GB of RAM, without a graphics processing unit. The implementation is done in python using TensorFlow 1.5.0. Classification performance is reported in terms of sensitivity ($S_e$) and specificity ($S_p$) of detecting abnormal heart sounds. These metrics are defined in terms of true positive ($TP_{ab}$), true negative ($TN_{ab}$), false positive ($FP_{ab}$) and false negative ($FN_{ab}$) as:

$$S_e = \frac{TP_{ab}}{TP_{ab} + FN_{ab}}$$

$$S_p = \frac{TN_{ab}}{TN_{ab} + FP_{ab}}$$

Below table 2 shows the performance comparison of the present disclosure with three open source abnormal heart sounds detection algorithms designed based on supervised learning. Learning models in the three open source abnormal heart sounds detection algorithms are based on the PhysioNet Challenge 2016 dataset. The present disclosure outperforms over the three open source abnormal heart sounds detection algorithms.

TABLE 2

| | | PASCAL | | University of Michigan | | In-house dataset | |
| --- | --- | --- | --- | --- | --- | --- | --- |
| Authors | Method | $S_e$ | $S_p$ | $S_e$ | $S_p$ | $S_e$ | $S_p$ |
| Potes et al. | AdaBoost and CNN | 0.81 | 0.84 | 0.95 | 0.97 | 0.90 | 0.93 |
| Zabihi et al. | Ensemble of SVMs | 0.84 | 0.86 | 0.97 | 1.0 | 0.89 | 0.92 |
| Kat et al. | Regularized Neural Net | 0.79 | 0.80 | 0.95 | 0.95 | 0.85 | 0.91 |
| Present disclosure | Semi Supervised, VAE | 0.89 | 0.90 | 0.99 | 1.0 | 0.91 | 0.92 |

In accordance with the present disclosure, as seen from the experimental evaluation also, the semi-supervised learning model 300A is generated without any training data related to the heart disease types for the training. Hence the requirement of the training datasets covering all heart disease types is avoided. Further, the semi-supervised learning model may accurately identify the presence of the abnormal heart sounds, by analyzing spectrographic properties of the subject to be monitored. The system 100 is adaptive, simple in design and flexible. Since the system 100 can be used as a portable or handheld, it can be used not only in medical care units and hospitals, but also at home.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims.

It is to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims (when included in the specification), the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A processor-implemented method comprising the steps of:

receiving, via one or more hardware processors, a plurality of normal heart sound signals, from an input data source, wherein each normal heart sound signal of the plurality of normal heart sound signals is of a predefined time window, and indicative of normal heart condition;

pre-processing, via the one or more hardware processors, each normal heart sound signal, to obtain a plurality of normal spectrograms for the plurality of normal heart sound signals, wherein each normal spectrogram of the plurality of normal spectrograms comprises spectrographic properties associated with the normal heart sound signal;

generating, via the one or more hardware processors, a semi-supervised learning model trained with training data, wherein the training data comprises probability distribution of the spectrographic properties of each normal spectrogram of the plurality of normal spectrograms, and wherein the semi-supervised learning model is generated by:

transforming each normal spectrogram into a vector representation, to obtain a plurality of normal input vectors for the plurality of normal spectrograms;

determining a normal latent vector for each normal input vector, to obtain a plurality of normal latent vectors for the plurality of normal input vectors, using an encoder unit of the semi-supervised learning model, wherein each normal latent vector comprises a latent representation of the associated normal input vector in a predefined reduced dimension;

determining a normal reconstructed vector for each normal latent vector to obtain a plurality of normal reconstructed vectors for the plurality of normal latent vectors, using a decoder unit of the semi-supervised learning model, wherein each normal reconstructed vector among the plurality of normal reconstructed vectors comprises a reconstructed vector representation of the associated normal input vector; and minimizing an optimization function of the semi-supervised learning model by estimating a set of weights for each normal reconstructed vector of the plurality of normal reconstructed vectors, to obtain a minimized optimization function, wherein the optimization function is defined based on (i) a logarithmic cross entropy of the corresponding normal input vector and the corresponding normal reconstructed vector and (ii) a Kullback-Leibler (KL) divergence between the probability distribution of the corresponding normal latent vector, and a predefined Gaussian distribution with a predefined set of parameters comprising a predefined mean vector and a predefined variance vector;

receiving, via the one or more hardware processors, an input heart sound signal of a subject being monitored, from a sensor unit, wherein the input heart sound signal is of the predefined time window;

pre-processing, via the one or more hardware processors, the input heart sound signal of the subject being monitored, to obtain an input spectrogram, wherein the input spectrogram comprises the spectrographic properties of the input heart sound signal; and identifying, via the one or more hardware processors, presence of abnormal heart sounds of the subject being monitored, by analyzing the input spectrogram, using the semi-supervised learning model with the minimized optimization function, wherein identifying the presence of the abnormal heart sounds by analyzing the input spectrogram using the semi-supervised learning model, comprises:

transforming the input spectrogram into the vector representation, to obtain an input vector;

determining an input latent vector for the input vector, using the encoder unit of the semi-supervised learning model, wherein the input latent vector comprises the latent representation of the input vector;

estimating a second set of parameters for the input latent vector, based on the minimized optimization function of the semi-supervised learning model;

determining an anomaly score from the second set of parameters for the input latent vector; and identifying the presence of the abnormal heart sounds, based on the anomaly score and a predefined anomaly threshold score.

2. The processor-implemented method of claim 1, wherein pre-processing each normal heart sound signal, to obtain the plurality of normal spectrograms for the plurality of normal heart sound signals, comprises:
filtering each normal heart sound signal, using a low-pass filter with a predefined cut-off frequency to obtain a filtered normal heart sound signal;
perform a down sampling at a predefined down-sampling frequency, on the filtered normal heart sound signal, to obtain a down-sampled normal heart sound signal; and
transforming the down-sampled normal heart sound signal, using a Short-time Fourier Transform (STFT) technique to obtain the normal spectrogram for the corresponding normal heart sound signal.

3. The processor-implemented method of claim 1, wherein pre-processing the input heart sound signal of the subject being monitored, to obtain the input spectrogram, comprises:
filtering the input heart sound signal, using a low-pass filter with a predefined cut-off frequency to obtain a filtered input heart sound signal;
perform a down sampling at a predefined down-sampling frequency, on the filtered input heart sound signal, to obtain a down-sampled input heart sound signal; and
transforming the down-sampled input heart sound signal, using a Short-time Fourier Transform (STFT) to obtain the input spectrogram for the input heart sound signal.

4. The processor-implemented method of claim 1, wherein the semi-supervised learning model is a convolutional variational autoencoder comprising the encoder unit and the decoder unit,
wherein the encoder unit comprises 3 convolutional neural network (CNN) layers, each CNN layer of the encoder unit is associated with a batch normalization layer and a max-pooling layer; and
wherein the decoder unit comprises 4 convolutional neural network (CNN) layers, each CNN layer of the decoder unit is associated with the batch normalization layer and an up-sampling layer.

5. A system comprising:
a memory storing instructions;
one or more Input/Output (I/O) interfaces; and
one or more hardware processors coupled to the memory via the one or more I/O interfaces, wherein the one or more hardware processors are configured by the instructions to:
receive a plurality of normal heart sound signals, from an input data source, wherein each normal heart sound signal of the plurality of normal heart sound signals is of a predefined time window, and indicative of normal heart condition;
pre-process each normal heart sound signal, to obtain a plurality of normal spectrograms for the plurality of normal heart sound signals, wherein each normal spectrogram of the plurality of normal spectrograms comprises spectrographic properties associated with the normal heart sound signal;
generate a semi-supervised learning model trained with training data, wherein the training data comprises probability distribution of the spectrographic properties of each normal spectrogram of the plurality of normal spectrograms, and wherein the semi-supervised learning model is generated by:

transforming each normal spectrogram into a vector representation, to obtain a plurality of normal input vectors for the plurality of normal spectrograms;
determining a normal latent vector for each normal input vector, to obtain a plurality of normal latent vectors for the plurality of normal input vectors, using an encoder unit of the semi-supervised learning model, wherein each normal latent vector comprises a latent representation of the associated normal input vector in a predefined reduced dimension;
determining a normal reconstructed vector for each normal latent vector to obtain a plurality of normal reconstructed vectors for the plurality of normal latent vectors, using a decoder unit of the semi-supervised learning model, wherein each normal reconstructed vector among the plurality of normal reconstructed vectors comprises a reconstructed vector representation of the associated normal input vector; and
minimizing an optimization function of the semi-supervised learning model by estimating a set of weights for each normal reconstructed vector of the plurality of normal reconstructed vectors, to obtain a minimized optimization function, wherein the optimization function is defined based on (i) a logarithmic cross entropy of the corresponding normal input vector and the corresponding normal reconstructed vector and (ii) a Kullback-Leibler (KL) divergence between the probability distribution of the corresponding normal latent vector, and a predefined Gaussian distribution with a predefined set of parameters comprising a predefined mean vector and a predefined variance vector;
receive an input heart sound signal of a subject being monitored, from a sensor unit, wherein the input heart sound signal is of the predefined time window;
pre-process the input heart sound signal of the subject being monitored, to obtain an input spectrogram, wherein the input spectrogram comprises the spectrographic properties of the input heart sound signal; and
identify presence of abnormal heart sounds of the subject being monitored, by analyzing the input spectrogram, using the semi-supervised learning model with the minimized optimization function,
wherein identifying the presence of the abnormal heart sounds by analyzing the input spectrogram using the semi-supervised learning model, comprises:
transforming the input spectrogram into the vector representation, to obtain an input vector;
determining an input latent vector for the input vector, using the encoder unit of the semi-supervised learning model, wherein the input latent vector comprises the latent representation of the input vector;
estimating a second set of parameters for the input latent vector, based on the minimized optimization function of the semi-supervised learning model;
determining an anomaly score from the second set of parameters for the input latent vector; and
identifying the presence of the abnormal heart sounds, based on the anomaly score and a predefined anomaly threshold score.

6. The system of claim 5, wherein the one or more hardware processors are further configured to pre-process each normal heart sound signal, to obtain the plurality of normal spectrograms for the plurality of normal heart sound signals, by:

filtering each normal heart sound signal, using a low-pass filter with a predefined cut-off frequency to obtain a filtered normal heart sound signal;

perform a down sampling at a predefined down-sampling frequency, on the filtered normal heart sound signal, to obtain a down-sampled normal heart sound signal; and transforming the down-sampled normal heart sound signal, using a Short-time Fourier Transform (STFT) technique to obtain the normal spectrogram for the corresponding normal heart sound signal.

7. The system of claim 5, wherein the one or more hardware processors are further configured to pre-process the input heart sound signal of the subject being monitored, to obtain the input spectrogram, by:

filtering the input heart sound signal, using a low-pass filter with a predefined cut-off frequency to obtain a filtered input heart sound signal;

perform a down sampling at a predefined down-sampling frequency, on the filtered input heart sound signal, to obtain a down-sampled input heart sound signal; and transforming the down-sampled input heart sound signal, using a Short-time Fourier Transform (STFT) to obtain the input spectrogram for the input heart sound signal.

8. The system of claim 5, wherein the semi-supervised learning model is a convolutional variational autoencoder comprising the encoder unit and the decoder unit, wherein the encoder unit comprises 3 convolutional neural network (CNN) layers, each CNN layer of the encoder unit is associated with a batch normalization layer and a max-pooling layer; and wherein the decoder unit comprises 4 convolutional neural network (CNN) layers, each CNN layer of the decoder unit is associated with the batch normalization layer and an up-sampling layer.

9. A computer program product comprising a non-transitory computer readable medium having a computer readable program embodied therein, wherein the computer readable program, when executed on a computing device, causes the computing device to:

receive a plurality of normal heart sound signals, from an input data source, wherein each normal heart sound signal of the plurality of normal heart sound signals is of a predefined time window, and indicative of normal heart condition;

pre-process each normal heart sound signal, to obtain a plurality of normal spectrograms for the plurality of normal heart sound signals, wherein each normal spectrogram of the plurality of normal spectrograms comprises spectrographic properties associated with the normal heart sound signal;

generate a semi-supervised learning model trained with training data, wherein the training data comprises probability distribution of the spectrographic properties of each normal spectrogram of the plurality of normal spectrograms, and wherein the semi-supervised learning model is generated by:

transforming each normal spectrogram into a vector representation, to obtain a plurality of normal input vectors for the plurality of normal spectrograms;

determining a normal latent vector for each normal input vector, to obtain a plurality of normal latent vectors for the plurality of normal input vectors, using an encoder unit of the semi-supervised learning model, wherein each normal latent vector comprises a latent representation of the associated normal input vector in a predefined reduced dimension;

determining a normal reconstructed vector for each normal latent vector to obtain a plurality of normal reconstructed vectors for the plurality of normal latent vectors, using a decoder unit of the semi-supervised learning model, wherein each normal reconstructed vector among the plurality of normal reconstructed vectors comprises a reconstructed vector representation of the associated normal input vector; and minimizing an optimization function of the semi-supervised learning model by estimating a set of weights for each normal reconstructed vector of the plurality of normal reconstructed vectors, to obtain a minimized optimization function, wherein the optimization function is defined based on (i) a logarithmic cross entropy of the corresponding normal input vector and the corresponding normal reconstructed vector and (ii) a Kullback-Leibler (KL) divergence between the probability distribution of the corresponding normal latent vector, and a predefined Gaussian distribution with a predefined set of parameters comprising a predefined mean vector and a predefined variance vector;

receiving an input heart sound signal of a subject being monitored, from a sensor unit, wherein the input heart sound signal is of the predefined time window;

pre-processing the input heart sound signal of the subject being monitored, to obtain an input spectrogram, wherein the input spectrogram comprises the spectrographic properties of the input heart sound signal; and identifying, via the one or more hardware processors, presence of abnormal heart sounds of the subject being monitored, by analyzing the input spectrogram, using the semi-supervised learning model with the minimized optimization function, wherein identifying the presence of the abnormal heart sounds by analyzing the input spectrogram using the semi-supervised learning model, comprises:

transforming the input spectrogram into the vector representation, to obtain an input vector;

determining an input latent vector for the input vector, using the encoder unit of the semi-supervised learning model, wherein the input latent vector comprises the latent representation of the input vector;

estimating a second set of parameters for the input latent vector, based on the minimized optimization function of the semi-supervised learning model;

determining an anomaly score from the second set of parameters for the input latent vector; and identifying the presence of the abnormal heart sounds, based on the anomaly score and a predefined anomaly threshold score.

* * * * *